US005984682A

United States Patent [19]
Carlson

[11] Patent Number: 5,984,682
[45] Date of Patent: Nov. 16, 1999

[54] IMMEDIATE, LAMINATED LIGHT CURED DIRECT COMPOSITE BRIDGE AND METHOD

[76] Inventor: Ronald S. Carlson, 4211 Waialae Ave., Honolulu, Hi. 96816

[21] Appl. No.: 08/929,144

[22] Filed: Sep. 10, 1997

Related U.S. Application Data

[63] Continuation-in-part of application No. 08/545,372, Jan. 11, 1996, abandoned.

[51] Int. Cl.$^6$ .................................................. A61C 13/12
[52] U.S. Cl. ............................ 433/180; 433/167; 433/219
[58] Field of Search ..................................... 433/167, 172, 433/180, 181, 215, 76

[56] References Cited

U.S. PATENT DOCUMENTS

| | | | |
|---|---|---|---|
| 2,092,549 | 9/1937 | Craigo | 32/34 |
| 4,080,736 | 3/1978 | Kennedy | 433/167 |
| 4,172,323 | 10/1979 | Orlowski | 433/180 |
| 4,504,229 | 3/1985 | Garito et al. | 433/215 |
| 5,000,687 | 3/1991 | Yarovesky et al. | 433/180 |
| 5,120,224 | 6/1992 | Golub | 433/215 |
| 5,171,147 | 12/1992 | Burgess | 433/181 |
| 5,183,414 | 2/1993 | Czerniawski | 433/76 |
| 5,194,001 | 3/1993 | Salvo | 433/180 |

OTHER PUBLICATIONS

Breakthrough Bridgework, The Direct–Light–Cured–Composite–Bridge, Dr. Ronald S. Carlson, Jul. 16, 1996, Syntro–Research, Division of C.M.S., Inc.

Breakthrough Bridgework, Dr. Ronald S. Carlson, Feb. 27, 1996, Syntro–Research, Division of C.M.S., Inc.

Direct L.C. Composite Bridge, Dr. Ronald S. Carlson, Syntro–Research, Apr. 3, 1995.

*Primary Examiner*—John J. Wilson
*Attorney, Agent, or Firm*—Womble Carlyle Sandridge & Rice, PLLC

[57] ABSTRACT

A permanent dental bridge comprised entirely of composite material may be constructed directly, i.e., without laboratory assistance, either in situ or ex situ. In the in situ process, composite material is applied between abutment teeth in the patient's mouth, affixing wings are formed from the composite material, those wings respectively attaching to corresponding surfaces on the abutment teeth, and the composite material is cured. The steps of application and curing of composite material are successively repeated until a completed dental bridge, including a pontic portion, is formed entirely within the patient's mouth. The ex situ process is accomplished by fabricating a composite pontic, applying composite material between the patient's abutment teeth, curing the composite material, applying a lamination of additional composite material between the abutment teeth, inserting the composite pontic into the lamination, and curing the lamination. In either process, a gingival stent is utilized to act as a platform upon which the successive composite laminations may be formed and also, if employed immediately following tooth extraction, to act as a bandage. The stent is inserted into the patient's mouth before application of composite material between the abutment teeth, and is removed after formation of the completed bridge but prior to the contouring and finishing thereof.

11 Claims, 5 Drawing Sheets

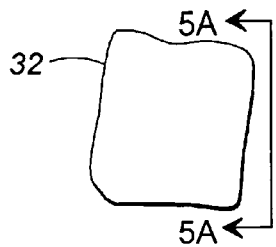
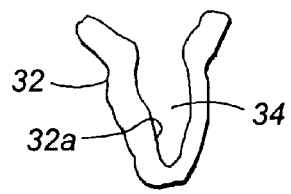
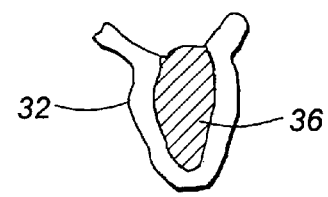
FIG. 5     FIG. 5A     FIG. 6
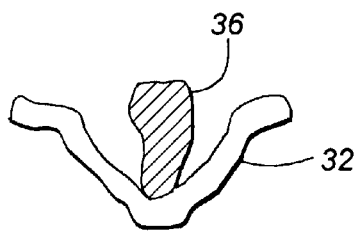
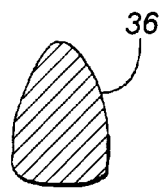
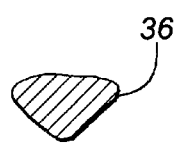
FIG. 7     FIG. 7A     FIG. 7B
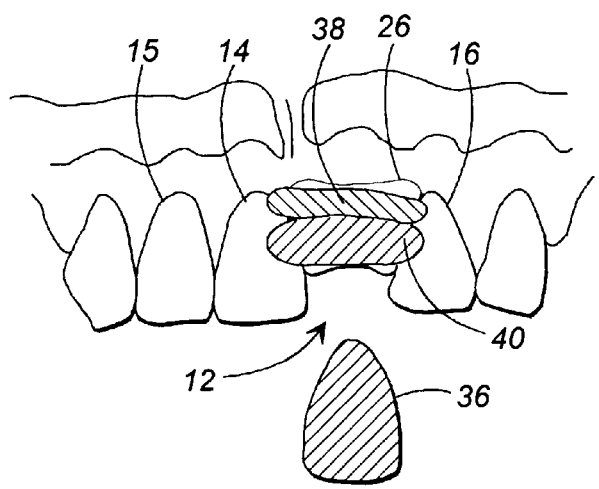
FIG. 9

IMMEDIATE, LAMINATED LIGHT CURED DIRECT COMPOSITE BRIDGE AND METHOD

RELATED APPLICATION DATA

This application is a continuation-in-part of application Ser. No. 08/545,372, filed Jan. 11, 1996, now abandoned.

BACKGROUND OF THE INVENTION

1. Field of the Invention

The invention is concerned with, generally, the domain of restorative and prosthetic dentistry, specifically, "fixed partial dentures," more commonly known as "fixed dental bridgework."

2. Description of the Relevant Art

Fixed dental bridgework has traditionally involved the following process: (1) during the first office visit by the patient, the dentist surgically reduces the anchor or "abutment" teeth on either side of the space (edentulous area) to be spanned by the bridgework; (2) the dentist makes an impression of the reduced abutment teeth and edentulous area; (3) the impression is sent to a laboratory for construction of a model to which the bridgework is conformed during fabrication; (4) metal "pontic" castings, a metal framework that holds the pontics, and attachment wings are fabricated; (5) in a special high temperature oven, porcelain may then be fused to the pontic forms, and to the metal attachment wings on each end of the metal bridge framework if desired, depending on the original bridgework design; (6) the bridgework is sent from the laboratory to the dentist, (7) during a second office visit by the patient, the dentist inserts and adjusts the bridgework in the patient's mouth; and (8) the dentist "permanently" cements the attachment wings or crowns on the ends of the bridgework to abutment teeth to fix the bridgework in place. Examples of the type of bridgework described above are shown in U.S. Pat. No. 5,194,001 to Salvo and in U.S. Pat. No. 5,000,687 to Yarovesky, et al.

A poor fit between the traditional bridgework and the abutment teeth cannot be discovered until the finished bridgework is inserted into the patient's mouth; a poor fit sometimes develops after a period of wear. To cure a poor fit, the bridgework must be removed from the patient's mouth, modified, then reattached. Sometimes, several iterations of attachment, removal, modification, reattachment are necessary, each requiring an office visit by the patient. Attachment wings or crowns run the range of mechanical and/or adhesive devices, such as screws, foils, films, screens, mastics, hooks, etc. Frequently, the reduction and/or process of attachment (especially the use of screws) injures the abutment teeth and can lead to caries, abscesses, and/or tooth death. Removal of the bridgework after cementation of the attachment wings to the abutment teeth sometimes injures the abutment teeth, or even requires their removal.

For decades there has been a quest for a more efficient, effective, and non-invasive means of replacing missing teeth in a fixed manner. Extraordinary efforts have been devoted to trying to devise methods that do not require cutting or otherwise mutilating the abutment teeth. Two of the most common methods devised to avoid reducing the abutment teeth are well known as the "Maryland bridge" and the "Rochette bridge." The Maryland bridge and the Rochette bridge are constructed with a metal framework of nickel-chromium and beryllium in the laboratory, etched with an acid medium or sandblasted on the tissue side surface of the attachment hooks, and then cemented to the natural abutment teeth with a polymer luting agent. Due to the inflexibility of the metal frame and the weak bond of the polymer to metal and to teeth, the attachment hooks separate from the abutment teeth. There are additional serious disadvantages with the Maryland and Rochette bridges. In the area of aesthetics, the underlying metal may "shine-through" the pontic surface, disrupting the color, hue, value and shade of the replacement tooth. The high-fusing-porcelain can rapidly abrade natural teeth opposite the bridge. The metallic content of the metal bridges sometimes precipitates allergic or even less understood impairment of the patient's health. There is a growing and real concern for the quality and quantity of metal used in dentistry and the deleterious effects on the bio-environment of the oral cavity. All three kinds of metals utilized in the previously mentioned bridges are bio-toxic to some degree. Nickel is known for its allergenic capacity and is an experimental carcinogen and equivocal tumor former. Chromium is a suspected carcinogen and an equivocal tumor producer. Beryllium is an equivocal neoplastic producer concerned with pulmonary problems that produce tumors and is an experimental carcinogen.

In additional to undesirable health side effects, laboratory fabricated porcelain/metal bridges have structural and aesthetic deficiencies Structurally, the metal can fracture, the porcelain can fracture, and/or the porcelain/metal fused interface can separate. All of these structural failures require removal of the bridge for repair. Aesthetically, after cementation of the bridge, changes over time in pontic color or shade versus natural teeth, or bridgework fit, require removal of the bridge. All these deficiencies of laboratory fabricated porcelain/metal bridges are difficult, if not impossible, to resolve. The chronic failure of the metal-polymer-tooth bond, and the other deficiencies noted above, have prompted research into other bridgework materials, namely those in the porcelain or composite groups.

These other attempts to eliminate or reduce the deficiencies noted above all rely, however, on the "indirect method," that is, fabrication of bridgework in a dental laboratory. To improve the strength of the bridgework to abutment tooth bond, doped methyl-acrylates, common known today as "composites," were introduced. Attempts have been made to affix a natural tooth or a fabricated pontic to abutment teeth utilizing webs of materials such as metal-bars, carbon-fiber-bars, screens, films, and foils made of various materials.

The indirect method has proven to be lengthy and complicated. Approximately ten laboratory steps are needed in the simplest traditional bridge construction, and with these steps come costs. Some methods are even more complex; for instance, U.S. Pat. No. 5,000,687 to Yarovesky et al. discloses an indirect method involving about 14 or 15 separate process steps. Furthermore, many indirect methods require the abutment teeth to be surgically reduced in some form; for example, the process disclosed in the aforementioned patent requires cutting and contouring of the lingual surfaces of the abutment teeth prior to bridge installation. U.S. Pat. No. 5,120,224 to Golub, seeking to eliminate or minimize the need for abutment tooth reduction, discloses a bridge structure wherein a thin fabric laminate may be internally sandwiched within the pontic/bridge. The fabric extends outwardly from the pontic/bridge for placement on abutment teeth and for bonding thereto by an adhesive. As stated in the Golub patent, however, the disclosed structure is intended to function only as a temporary bridge. Moreover, it has been found that the placement of a fabric or screen within composite material actually weakens, rather than strengthens, the bridge framework. All laboratory-based indirect methods are therefore relatively costly, time consuming, and ineffective.

U.S. Pat. No. 4,172,323 to Orlowski discloses a method for securing a previously-made pontic or a fixed bridge, wherein a thin film or screen is applied to respective abutment teeth surfaces. Adhesive is applied between the screens and the pontic/bridge to be installed, whereafter the pontic/bridge is installed and held in place while the adhesive cures. Orlowski, however, discloses that small undercuts are made in the enamel of the abutment teeth contact areas, so as to increase the area available for bonding and resistance to shear forces. Despite that attempt to increase contact areas, it has been found that these areas are still limited such that weakness of joints results. Consequently, the securement structure disclosed by Orlowski has been found to be temporary, i.e., lasting less than five years before failure.

Where tooth extraction is required before insertion of fixed dental bridgework, regardless of whether the bridgework has been constructed directly or indirectly, the traditional approach requires two to four months healing of the extraction site (alveolar socket) prior to bridge installation. The fabrication and installation of a fixed dental bridge during the same office visit as extraction of teeth from the area to be bridged has heretofore been regarded as impossible.

Accordingly, there is a need in the art for a method of directly producing a permanent dental bridge which eliminates invasive tooth preparation steps and which can be done during the same office visit as tooth extraction.

SUMMARY OF THE INVENTION

It is thus an object of the present invention to provide a method of constructing a dental bridge which overcomes the drawbacks associated with prior art methods.

It is a further object of the present invention to provide a direct method of constructing a permanent dental bridge which is efficient and inexpensive.

It is a further and more particular object of the present invention to provide a direct method of constructing a permanent dental bridge which can be accomplished in situ, that is, entirely within the patient's mouth, or instead ex situ, at least partially outside the patient's mouth.

It is an additional object of the present invention to provide a novel gingival stent which, in addition to functioning as a platform upon which successive composite laminations may be formed, acts as a bandage for the alveolar socket, thereby allowing tooth extraction and bridge construction to be accomplished in the same office visit.

These and other objects are accomplished by a method of constructing a dental bridge in situ, the dental bridge when completed occupying an edentulous space between a first abutment tooth and a second abutment tooth in a mouth of a patient, comprising the steps of applying composite material between the first and second abutment teeth, forming first and second affixing wings from the composite material, the affixing wings respectively attaching to corresponding surfaces on the first and second abutment teeth, and curing the composite material, whereby the dental bridge is constructed entirely within the mouth of the patient. After the aforementioned curing step, additional composite material is applied between the abutment teeth, from which the first and second affixing wings continue to be formed, and the additional composite material is cured. These latter steps are successively repeated, thus forming built-up laminations of composite material, until the dental bridge, including a pontic portion, is formed.

The foregoing objects are also accomplished by a method of constructing a dental bridge ex situ, the dental bridge when completed occupying an edentulous space between a first abutment tooth and a second abutment tooth in a mouth of a patient, comprising the steps of fabricating a composite pontic, applying composite material between the abutment teeth, curing the composite material, applying a lamination of additional composite material between the abutment teeth, inserting the composite pontic into the lamination, and curing the lamination.

In either the in situ process or the ex situ process, a novel gingival stent is utilized to act as a platform upon which the successive composite laminations may be formed and also, if employed immediately following tooth extraction, to act as a bandage. The stent is inserted into the patient's mouth before application of composite material between the abutment teeth, and is removed after formation of the completed bridge but prior to the contouring and finishing thereof. The novel gingival stent comprises a base, the base having a facial margin into which concave sections are formed to snugly fit around lingual surfaces of the abutment teeth and teeth adjacent thereto, and a ridge extending substantially vertically from the base, the ridge covering a gingival surface in the edentulous space when the stent is placed within the mouth.

The objects of the invention are additionally accomplished by a dental bridge comprising a pontic comprised of composite material, and affixing wings comprised of the same composite material as the pontic, the affixing wings respectively attached at one side to the pontic and respectively attaching at another side to corresponding surfaces on the first and second abutment teeth.

The foregoing objects are also accomplished by providing a dental bridge prepared by the process of applying composite material between the first and second abutment teeth, forming first and second affixing wings from the composite material, the affixing wings respectively attaching to corresponding surfaces on the first and second abutment teeth, and curing the composite material. Additionally accomplishing the foregoing objects is a dental bridge prepared by the process of fabricating a composite pontic, applying composite material between the first and second abutment teeth, curing the composite material, applying a lamination of additional composite material between the first and second abutment teeth, inserting the composite pontic into the lamination, and curing the lamination.

BRIEF DESCRIPTION OF THE DRAWINGS

FIG. 5 is a front view of a cooled, empty wax mold formed from the layer of wax illustrated in FIGS. 4 & 4A.

FIG. 5A is a side elevation view of the mold, taken along line 5A—5A in FIG. 5.

FIG. 6 is a side elevation view of the mold shown in FIGS. 5 & 5A, additionally showing a resin polymer material filled within the mold.

FIG. 7 is a side elevation view of the wax mold being opened and separated from cured resin polymer material, which now forms a pontic.

FIG. 7A is a front view of the pontic shown in FIG. 7.

FIG. 7B is a plan view of the pontic shown in FIG. 7.

FIG. 9 is a front view of a dental arch similar to FIG. 3A, additionally showing intended placement of pontic in the edentulous space of the dental arch, in accordance with the ex situ process of the present invention.

DETAILED DESCRIPTION OF THE BEST MODE

The "immediate, laminated, light cured direct composite bridge" comprises one or more "direct composite pontics," a bridge substructure, and affixing wings that are integrally fabricated and affixed in place between two or more abutment teeth in an immediate process; moreover, abutment teeth need not be reduced. "Composite" means light curable composite dental materials, such as various formulations of a colloid paste of methyl methacrylate resin and silica commonly available from dental supply houses, preferably of the type made commercially available from Prisma APH of Milford, Delaware. "Composite pontic" means a false tooth ("pontic") made only of light cured composite." "Direct composite pontic" means a composite pontic made without dental laboratory assistance by application and light curing of successive laminations of composite, either in situ or ex situ, as explained below. "Immediate" means that the process of fabricating and affixing the composite bridge can be completed in one office visit. The fabrication of an individual composite pontic can be performed either completely within the patient's mouth (called "in situ" fabrication) or outside the patient's mouth (called "ex situ" fabrication). The "direct composite bridge" contrasts with traditional "indirect" methods of dental bridge construction that require fabrication of bridgework in a dental laboratory.

The in situ fabrication of an immediate laminated, light cured composite bridge will be described in detail first, followed by a detailed description of the ex situ fabrication of such a bridge.

Figure 1:
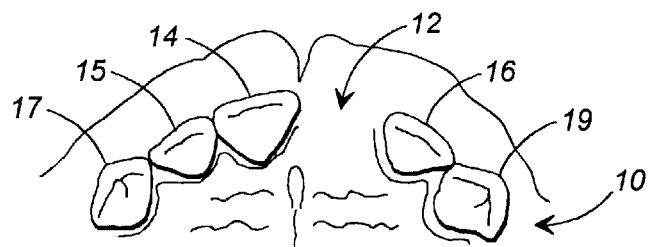
FIG. 1 is a palatal view of a dental arch of a mouth of a patient, showing an edentulous space defined between first and second abutment teeth.
Figure 1A:
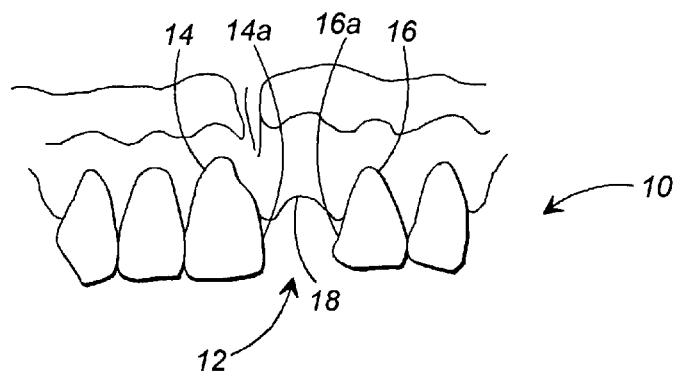
FIG. 1A is a front view of the dental arch shown in FIG. 1.

Referring to FIGS. 1 & 1A, an upper dental arch 10 of a patient's mouth is shown. Dental arch 10 includes a row of teeth, one of which has been removed, thereby leaving an edentulous (toothless) space 12 between abutment teeth, namely, a first abutment tooth 14 and a second abutment tooth 16. The edentulous space 12 is shown in FIG. 1A as exposing a gingival surface (or alveolar ridge) 18 of the alveolar socket associated with the missing tooth. If that missing tooth has been extracted immediately prior to the time of bridge fabrication and installation, then it has been found that the use of a gingival stent, to be described below, is particularly advantageous.

Figure 2:
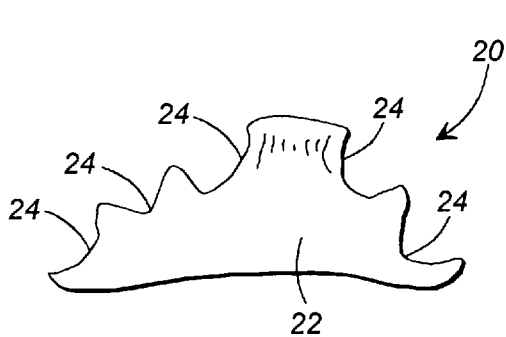
FIG. 2 is a palatal view of a gingival stent constructed according to the present invention.
Figure 2A:
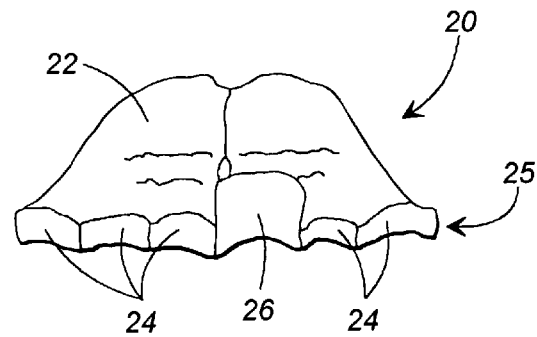
FIG. 2A is a front view of the gingival stent shown in FIG. 2.
Figure 2B:
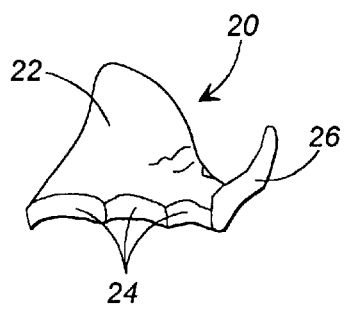
FIG. 2B is a side view of the gingival stent shown in FIG. 2.

Referring to FIGS. 2, 2A & 2B, to control, form, and contour the flow of uncured composite laminations over the edentulous space 12 (FIGS. 1 & 1A) prior to solidification by light curing, a novel infra pontic gingival stent 20 (hereinafter referred to as "gingival stent") is used. The gingival stent 20 is installed commencing approximately five minutes after tooth extraction is completed. The gingival stent 20 has a dual function: it acts as a bandage stabilizing the clotting process in the alveolar socket (if tooth extraction occurs during the same office visit as bridge formation), and it also serves as a platform upon which the composite bridge is fabricated according to steps to be described in detail later herein.

The gingival stent 20 includes a base 22 having a facial margin 25 into which a plurality of concave sections 24 are formed. Concave sections 24 are dimensioned to snugly fit around lingual surfaces of the abutment teeth 14, 16 and teeth adjacent thereto (such as teeth 15, 17, 19 in FIG. 1). A ridge 26 extends substantially vertically from the facial margin 25 of the base 22; its purpose is to cover the gingival surface 18 in the edentulous space 12 (FIGS. 1 & 1A) when the gingival stent 20 is placed within the patient's mouth. Preferably, ridge 26 is formed integrally with the base 22 such that the ridge 26 and the base 22 form a one-piece structure.

The gingival stent 20 is preferably constructed with vinyl polysiloxane impression material or equivalent, such as that commercially available as type "o" putty from GC America, Inc. of Chicago, Ill. under the trademark EXAFLEX. The material is mixed in hand and adapted to the lingual surfaces of the abutment teeth and adjacent teeth, molded interdentally (i.e., in the patient's mouth) where possible, to cover the entire edentulous ridge to the facial cervical, defined as the substantially straight datum line D (FIG. 3A) passing the through the cervical surface (the area where the gum meets the tooth) of each of the abutment teeth 14, 16. Such coverage will enable the facial margin 25 of gingival stent 20 to be even, in a horizontal attitude, with the tooth cervical areas. The setting agent in the polysiloxane material causes the gingival stent 20 to solidify as formed. When set, the gingival stent 20 is removed and contoured with a fine fluted finishing bur to minimal acceptable thickness. During the months that follow the extraction, the alveolar ridge 18 (FIG. 1A) gradually shrinks as it heals; this shrinkage exposes a space gingival to the tissue side of the pontic. That space is easily closed by applying additional composite in the space and light curing the composite to the existent bridge. Some space should be left for hygienic irrigation, however.

In the first step of the in situ method of direct composite bridge fabrication according to the present invention, each affixation surface of each abutment tooth 14, 16 is etched, preferably with a 35% phosphoric acid gel for about twenty seconds. As used herein, the term "affixation surface" includes proximal surfaces 14a, 16a (FIG. 1A), lingual surfaces 14b, 16b (FIG. 3), and facial surfaces 14c, 16c (FIG. 3A) of abutment teeth 14 & 16.

Figure 3:
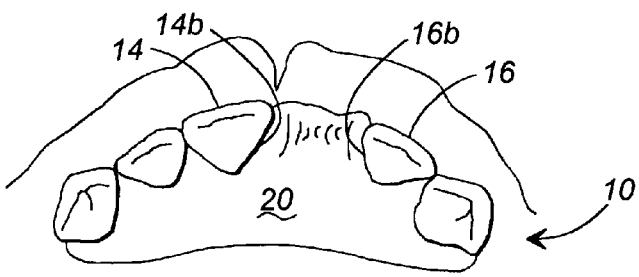
FIG. 3 is a palatal view of the dental arch shown in FIG. 1, with the gingival stent shown in FIGS. 2–2B positioned therein.
Figure 3A:
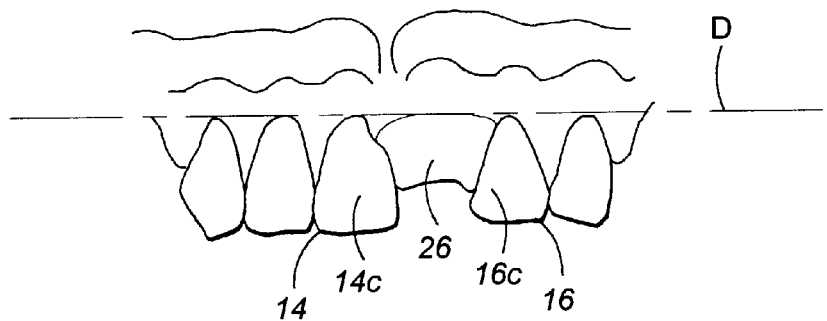
FIG. 3A is a front view of the dental arch with the gingival stent positioned therein.

Referring to FIGS. 3 & 3A, the gingival stent 20 is inserted into the patient's mouth before application of any composite material. The inserted gingival stent 20 is shown in FIG. 3 as fitting snugly behind all the teeth within the patient's dental arch 10 FIG. 3A additionally shows the ridge 26 of the gingival stent 20 covering the previously-exposed alveolar ridge 18 (FIG. 1A), as well as being contiguous with both abutment teeth 14, 16. As will be explained in detail herein, the gingival stent 20 is removed no later than the completion of the direct composite bridge.

Figure 12:
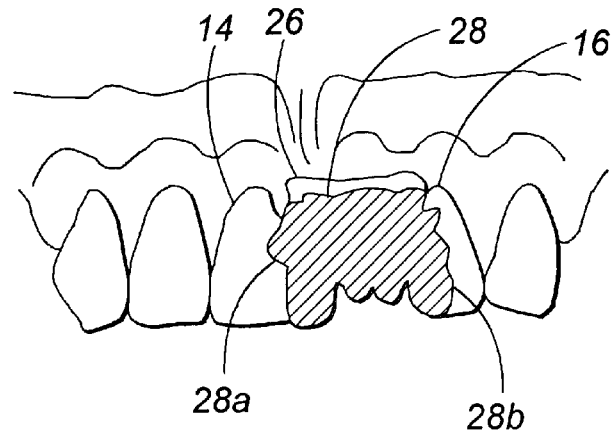
FIG. 12 is a front view of a dental arch similar to FIG. 3A, additionally showing the application of composite material across edentulous space, in accordance with the in situ process of the present invention.

Referring to FIG. 12, composite material 28 is shown as having been applied between the affixation surfaces of the abutment teeth 14, 16. Preferably, the composite material 28 is applied in a series of beaded strings leading from one abutment tooth, across the ridge 26 of gingival stent 20, and to the other abutment tooth, each string being no thicker than 1–2 mm to ensure proper photo-curing. The applied composite material 28 is smoothed with various instruments and shaped so as to begin to form a first affixing wing 28a on the affixation surface of first abutment tooth 14, and a second affixing wing 28b on the affixation surface of the second abutment tooth 16. The ridge 26 of the stent 20 is shown acting as a platform for the placement of the composite material 28, meaning that the composite material occupying the edentulous space 12 contacts the front face of ridge 26 during the bridge fabrication process. Using the gingival stent 20, it has been found that the lamination area for each abutment tooth can exceed 1 cm$^2$, thus providing an exceptionally strong bridge structure. The composite material 28 is then cured, preferably with a light source (not shown). Following that curing step, additional composite material is applied between the abutment teeth 14, 16, and the first and second affixing wings 28a, 28b continue to be formed from that material, which is then cured. These steps of applying additional composite material, forming first and second affixing wings, and curing the additional composite material are successively repeated, thereby simultaneously forming built-up laminations of composite material and the composite bridge substructure.

Figure 13:
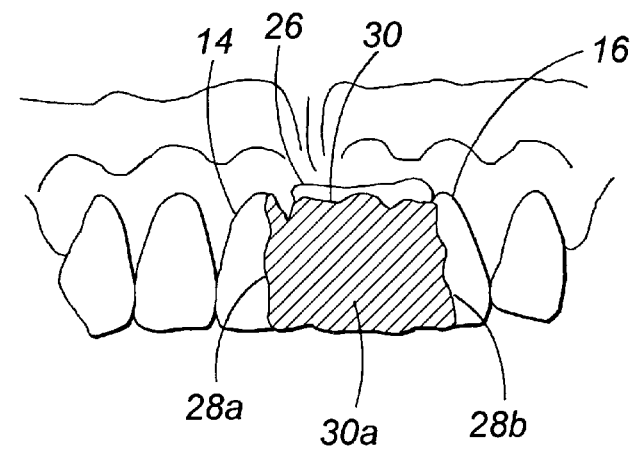
FIG. 13 is a front view similar to FIG. 12, showing completion of a dental bridge, but prior to removal of a gingival stent, in accordance with the in situ process of the present invention.

Referring to FIG. 13, the build-up of laminations ceases when a dental bridge 30, including a pontic portion 30a, has been formed. The bridge 30 resulting from this novel process of fabrication is a solid, acceptably flexible, high strength structure that integrates pontics, affixing wings, and substructure. Once bridge 30 has been formed, the gingival stent 20, including its ridge 26, is removed from the patient's mouth, and is then discarded. Stent removal is made possible by the fact that the gingival stent 20, being constructed of material differing from the composite material comprising the bridge 30, does not chemically fuse or weld to the composite. Without such adhesion, the gingival stent 20, once the composite has been cured, easily slides from beneath the bridge pontic portion and from around the abutment teeth 14, 16 and teeth adjacent thereto.

As a final step in the in situ process, the bridge 30 is contoured and finished, meaning that the "over-bulked" composite is trimmed with various rotary instruments such as diamond burs, fine fluted finishing burs, and rubber wheels, then finished with polishing paste.

In the ex situ process, which will now be described in detail, a composite pontic must first be fabricated outside the patient's mouth.

Figure 4:
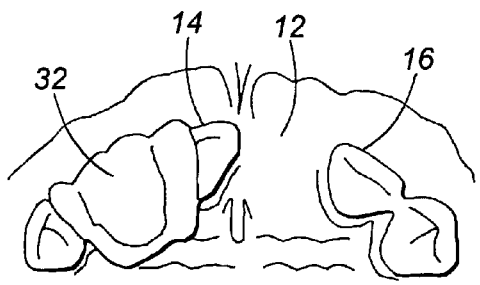
FIG. 4 is a palatal view of a dental arch with a layer of wax pressed upon a lateral incisor within the arch.
Figure 4A:
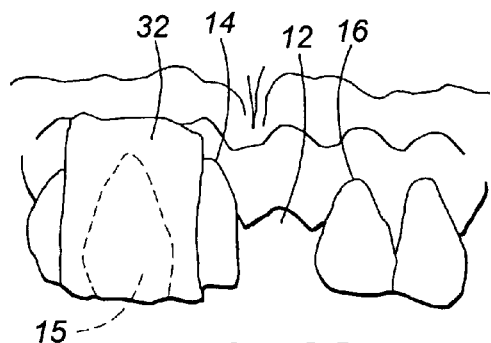
FIG. 4A is a front view of a dental arch with a layer of wax pressed upon a lateral incisor within the arch.

In FIGS. 4 & 4A, a layer of warm wax is placed over another tooth, such as lateral incisor 15, within dental arch 10, thereby forming a wax mold 32 of lateral incisor 15. The wax used to comprise mold 32 is preferably a number 3 wax, commercially available from Miles, Inc. of South Bend, Ind. under the trademark MODERN MATERIALS.

Referring to FIGS. 5, 5A, & 6, the mold 32 is removed from the lateral incisor 15 and is allowed to cool. As seen in FIG. 5A, the mold 32 has a somewhat V-shaped profile, whereby an internal wall 33a of the mold 32 defines an internal chamber 34. A layer of un-filled resin polymer is placed within mold 32 and is then cured. The layer of un-filled resin polymer acts as a lubricant on wall 33a and allows for ease of removal of the completed pontic from the mold 32, to be described later herein. Next, layers of a filled resin polymer are successively placed within the mold 32, preferably at a thickness each of 1 mm to 2 mm, and cured until a completed composite pontic 36 is formed within the mold 32, as shown in FIG. 6.

As depicted in FIGS. 7, 7A, & 7B, the mold 32 is peeled back, or removed, from the completed pontic 36, which is seen as being substantially identical to the lateral incisor 15 from which the mold 32 was formed. Although these figures show a single pontic 36, the term "pontic", as used in the claims stated herein, shall be construed to mean a plurality of pontics (in the patient is initially missing more than one tooth), as well as a singular pontic.

Figure 8:
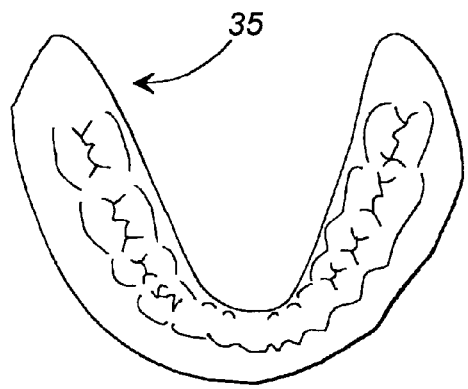
FIG. 8 is a plan view of a crown form which is used to fabricate a pontic in accordance with a modified ex situ process of the present invention.
Figure 8A:
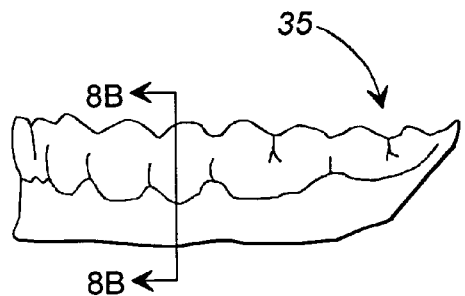
FIG. 8A is a side elevation view of the crown form shown in FIG. 8.
Figure 8B:
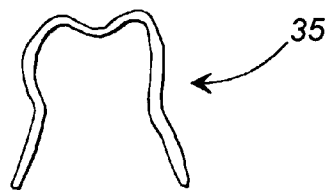
FIG. 8B is a sectional elevation view of the crown form taken along line 8B—8B in FIG. 8A.

Referring to FIGS. 8, 8A, & 8B, the pontic fabrication process can employ a crown form 35 instead of the mold 32, such that mold formation steps would be eliminated, with polymer deposition and curing steps occurring identically in the manner described with regard to the wax mold process.

Custom-fabricating the pontic 36 in the manners hereinabove described has been found to be advantageous over merely selecting a pontic from commercially available stock, because stock pontics will not chemically adhere to affixing wings or a bridge substructure, which are formed of composite material according to the present invention.

Figure 10:
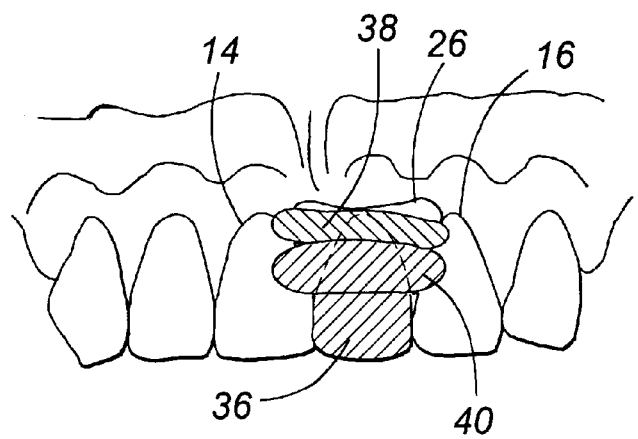
FIG. 10 is a front view similar to FIG. 9, except that it shows actual placement of the pontic in the edentulous space.

In FIGS. 9 & 10, the affixation surfaces of the abutment teeth 14, 16 have been prepared, and the gingival stent 20 (including ridge 26) inserted, in the same manner as previously described with regard to the in situ process. Here, the completed pontic 36 is aligned with the edentulous space 12, as shown in FIG. 9. Next, an initial layer of composite material 38 is seen as having been applied between the first and second abutment teeth 14, 16, respectively. Layer 38 is then cured, whereafter a lamination of additional composite material 40 is applied between the abutment teeth; curing does not immediately follow; rather, the composite pontic 36 is first inserted into the uncured lamination 40, as seen in FIG. 10. Once this occurs, lamination 40 is cured. If desired, the gingival surface of composite pontic 36 may be serrated, or roughened, while partially cured to create more surface area with which to bond the pontic to one or more uncured composite laminations on the bridge substructure.

Figure 11:
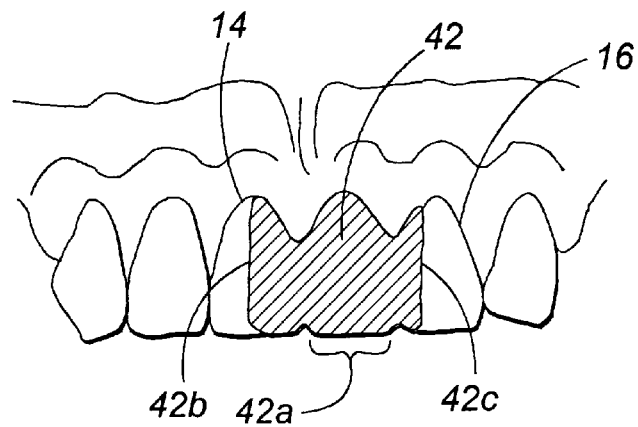
FIG. 11 is a front view similar to FIG. 10, except that it shows a completed bridge constructed in accordance with the ex situ process of the present invention.

Referring to FIG. 11, successive additional laminations of composite material and curing thereof result in a completed dental bridge 42, including pontic portion 42a and wings 42b, 42c. The ex situ process is then completed by contouring and finishing the bridge 42 in the same manner as that described with regard to the in situ process.

It is therefore seen that a direct, immediate, light-cured direct composite dental bridge may be efficiently constructed in a manner which results in several advantages, namely: a) no tooth preparation by extensive enamel reduction which prevents pulpal death leading to complex endodontic treatment; b) often no need for anesthetic injections; c) no need for impressions; d) no need for temporary bridges; e) aesthetic input from the patient at the time of bridge lamination and completion; f) elimination of casting or porcelain errors within the laboratory; g) obviates errors in occlusion (bite) due to articulation errors and model inaccuracies; h) revolutionary "one-phase" material application; i) no laboratory procedures saving time, materials, and expense; j) no cementation of the bridge framework to the abutment teeth after the indirect construction of the bridge framework with the pontic; k) one appointment only for the patient; l) no metal corrosive activity or ionization, thus preventing metal ion bio-contamination; and, m) the bridge will not need to be removed for repair or correction of shade, since all addition or shade changes may be made directly to the existing substrate at any time in the future.

As the above description is merely exemplary in nature, being merely illustrative of the invention, many variations will become apparent to those of skill in the art. Such variations, however, are included within the spirit and scope of this invention as defined by the following appended claims.

That which is claimed:

1. A method of constructing a dental bridge in situ, said dental bridge when completed occupying an edentulous space between a first abutment tooth and a second abutment tooth in a mouth of a patient, comprising the steps of:

inserting a gingival stent into the mouth;

covering an alveolar ridge in the mouth with a portion of said gingival stent;

occupying the edentulous space with a front face of said portion while said gingival stent is in the mouth;

applying composite material onto an affixation surface of the first abutment tooth, across said front face, and onto an affixation surface of the second abutment tooth; and curing said composite material;

whereby a dental bridge is constructed entirely within the mouth of the patient.

2. The method set forth in claim 1, further comprising the steps of:

applying additional composite material onto the affixation surface of the first abutment tooth, across said front face, and onto the affixation surface of the second abutment tooth after said step of curing said composite material;

curing said additional composite material; and successively repeating said steps of applying additional composite material and curing said additional composite material, thereby forming built-up laminations of composite material, until said dental bridge, including a pontic portion, is formed.

3. The method set forth in claim 1, further comprising the steps of removing said gingival stent, and contouring and finishing said dental bridge after said step of removing said gingival stent.

4. The method set forth in claim 1, further comprising the step of etching the affixation surfaces before said step of applying composite material.

5. A method of constructing a dental bridge ex situ, said dental bridge when completed occupying an edentulous space between a first abutment tooth and a second abutment tooth in a mouth of a patient, comprising the steps of:

fabricating a composite pontic;

inserting a gingival stent into the mouth;

covering an alveolar ridge in the mouth with a portion of said gingival stent;

occupying the edentulous space with a front face of said portion while said gingival stent is in the mouth;

applying composite material onto an affixation surface of the first abutment tooth, across said front face, and onto an affixation surface of the second abutment tooth;

curing said composite material;

applying a lamination of additional composite material between the first and second abutment teeth;

inserting said composite pontic into said lamination; and curing said lamination.

6. The method set forth in claim 5, further comprising the steps of:

removing said gingival stent from the mouth of the patient after said dental bridge is formed; and contouring and finishing said dental bridge after said step of removing said gingival stent.

7. The method set forth in claim 5, further comprising the step of etching the affixation surfaces of the first and second abutment teeth before said step of applying composite material.

8. The method set forth in claim 5, wherein said step of fabricating said composite pontic comprises the steps of:

placing a layer of wax over a third tooth within a same arch as the first and second abutment teeth, thereby forming a wax mold of the third tooth;

removing said mold from the third tooth;

cooling said mold;

placing a layer of un-filled resin polymer within said mold;

curing said layer;

placing a layer of filled resin polymer within said mold;

curing said layer of filled resin polymer;

repeating said steps of placing a layer of filled resin polymer within said mold and of curing each such layer of filled resin polymer until a completed composite pontic is formed within said mold; and removing said completed composite pontic from said mold.

9. The method set forth in claim 5, wherein said step of fabricating said composite pontic comprises the steps of:

placing a layer of un-filled resin polymer within a crown form;

curing said layer of said un-filled resin polymer;

placing a layer of filled resin polymer within said crown form;

curing said layer of filled resin polymer;

repeating said steps of placing a layer of resin polymer within said crown form and of curing each such layer of filled resin polymer until a completed composite pontic is formed within said crown form; and removing said completed composite pontic from said crown form.

10. A gingival stent for facilitating the direct construction of a dental bridge which will occupy an edentulous space between a first abutment tooth and a second abutment tooth in a mouth of a patient, comprising:

a bases said base having a facial margin into which concave sections are formed to snugly fit around lingual surfaces of the abutment teeth and teeth adjacent thereto; and a ridge extending substantially vertically from said base, said ridge covering a gingival surface in the edentulous space when said stent is placed within the mouth.

11. The gingival stent set forth in claim 10, wherein said gingival stent is constructed from a vinyl polysiloxane impression material.

* * * * *